United States Patent [19]

Reid

[11] Patent Number: 4,645,669

[45] Date of Patent: Feb. 24, 1987

[54] CULTURING AND EMPLACEMENT OF DIFFERENTIATED CELLS IN VIVO

[75] Inventor: Lola C. M. Reid, Mt. Vernon, N.Y.

[73] Assignee: Albert Einstein College of Medicine of Yeshiva University, Bronx, N.Y.

[21] Appl. No.: 432,552

[22] Filed: Oct. 4, 1982

[51] Int. Cl.⁴ .............................................. A61K 35/12
[52] U.S. Cl. ......................................... 424/95; 435/1; 435/240; 514/2; 424/106
[58] Field of Search ...................... 424/177, 95; 435/1, 435/240

[56] References Cited

U.S. PATENT DOCUMENTS

| | | | |
|---|---|---|---|
| 4,016,036 | 4/1977 | Green et al. | 435/241 |
| 4,299,819 | 11/1981 | Eisinger | 435/241 |
| 4,485,096 | 11/1984 | Bell | 424/95 |
| 4,501,815 | 2/1985 | Reid et al. | 435/284 |

OTHER PUBLICATIONS

Oliver et al.,–Chem. Abst. vol. 96 (1982) pp. 140, 800t.
Oliver et al.,–Chem. Abst. vol. 95 (1981) p. 148332s.
Baumgartner–Chem. Abst. vol. 94 (1981) 20373t.

*Primary Examiner*—Sam Rosen

[57] ABSTRACT

A method and culture solution are disclosed which enable in vivo emplacement of differentiated cells derived from in vitro culturing of differentiated cells, with significant retention of their differentiated character. In an alternative embodiment, in vivo culturing of differentiated cells is contemplated. Through the use of extracellular matrix fibers, specifically derived from connective tissue, as culture substrates, the method also discloses the isolation of the connective tissue fibers and their preparation as a culture substrate. This method provides significantly higher survival and attachment rates, and often significantly improved growth properties for in vivo or in vitro cultures of differentiated cells, especially epithelial, over the current methods for culturing these cells. This method also significantly enables certain differentiated cells to retain much of their normal enzymatic activities, and furthermore, this method enables certain differentiated cells to retain to a high degree, their ability to secrete substances, such as hormones.

22 Claims, No Drawings

CULTURING AND EMPLACEMENT OF DIFFERENTIATED CELLS IN VIVO

CROSS-REFERENCE TO RELATED APPLICATIONS

The present application is related to co-pending and commonly owned U.S. patent applications Ser. No. 089,167 filed Oct. 29, 1979, to issue on Oct. 5, 1982 as U.S. Pat. No. 4,352,887; Ser. No. 307,311 filed Sept. 30, 1981 which was abandoned in favor of a continuation application Ser. No. 499,675, filed June 6, 1983; and Ser. No. 392,323 filed June 25, 1982, which issued on Feb. 26, 1985 as U.S. Pat. No. 4,501,815.

BACKGROUND OF THE INVENTION

1. Field of the Invention

The in vivo culturing of differentiated cells, and/or the in vitro culturing of differentiated cells, followed by emplacement of the cells in vivo.

2. Description of the Prior Art

Among the pertinent prior art in this field may be mentioned the use of a matrix in the treatment and healing of bone fractures, e.g. a broken hip, or for plastic surgery of any sort, i.e. if it is desired to stimulate a patient's body to respond; e.g., to heal a tissue, a wound, a burn, or the like, a matrix is used to solicit the right kind of growth. With regard to the use of a matrix, e.g. for bones, a prior art matrix and technique entails the grinding up of bone matter. The material is put in EDTA (ethylene diamine tetra acetic acid) to remove calcium and to demineralize; however, this technique entails and includes a non-isolated matrix. In one such technique, the material is comminuted, e.g. ground up, and is sprinkled or otherwise put like a salt into the wound, or break, or fracture, e.g. a broken hip; the paste or powder gets pasty and is sealed over. The bone will grow through and within the paste, because the matrix originates from bone. An orthopedic surgery application indicates that using a matrix is a good tool for plastic surgeons, and is efficacious in getting the bone to heal. Analogous techniques are known for acne pits. Here collagens are employed to fill in the acne pits and promote uniform skin growth. Collagens have also been disposed in teeth to promote bone formation.

Among the prior art journal articles pertinent to this field may be mentioned, e.g. with regard to the healing of bones, Rath, Hand, and Reddi, *Developmental Biology*, V. 85 (1981), pp. 89–98; Reddi et al, *Proc. Nat. Acad. Sci.*, V. 74 (1977), pp. 5589–5592; Reddi and Anderson, *J. Cell Biology*, V. 69 (1976), pp. 557–572; Rath and Reddi, *Nature*, V. 278 (1979), pp. 855–857; Lancet, 1981, V. 1, pp. 959–963; *Clinical Orthopedics*, V. 154, pp. 97–113; and Proc. Nat. Acad. Sci., V. 69 (1972), pp. 1601–1605.

It is known that successful in vitro culturing of differentiated cells remains especially difficult and elusive when utilizing current cell culture techniques. The lack of established and stable, normal and malignant cultures of differentiated cells has severaly hampered certain fields of research, especially cancer studies and treatment.

Currently, the culturing of cells is done primarily with one of three methods:

Organ culture: maintenance of organs separated from their central vascular supply, but with the organ, as an entity, left intact.

Tissue culture: culture of tissues or fragmented organs. The "sociocellular" relationships of the tissue architecture are preserved.

Cell culture: culture of an individual cell type divorced from other cell types.

A marked difference in response of explanted cells occurs when they are cultured by cell rather than organ or tissue culture techniques. Methods which retain tissue architecture permit retention of tissue-specific functions including hormonal and pharmacological responses. However, the tissue normally degenerates within a few weeks, due primarily to difficulties in nutrient and waste products exchange. Cell culture procedures overcome this limitation since they use explanted tissues which are disaggregated into single cells. The cells are adapted to grow as a monolayer on a solid-state support such as treated plastic, or as a cell suspension, and can be maintained in culture for extended periods. Nutrients are supplied by a liquid medium of defined basal composition supplemented with one of various sera. Ideally, one isolates a clonal cell line, i.e. a single cell whose progeny are maintained in continuous cell culture. There is genetic uniformity, easier maintenance of the cells, and reduction of variables associated with a multicell culture system. Nevertheless, cell culture procedure usually results in distortion of cellular phenotype and karyotype; normal cells rarely adapt as permanent cell lines without developing abnormal karyotypes or losing tissue-specific functions; malignant cells adapt more easily than do benign tumor cells or normal cells; and fibroblasts or stromal components become established preferentially over epithelial cells. The difficulties of establishing differentiated cells in cell culture have been attributed to many causes. These include an inadequately defined basal medium; inadequately defined hormone requirements; the static conditions of cell culture in which nutritional and oxygen gradients develop and limit the growth and functioning of cells with strict nutritional and oxygen requirements; and loss of or damage of cell-cell junctions, perhaps essential in growth and/or differentiation or both by the cell culture procedures of mechanical and enzymic dissociation into single cell suspensions. Undoubtedly all of these have contributed to the impasse in maintaining differentiated cells in cell culture. Yet despite progress on these various fronts, the goal of routinely culturing normal differentiated cells remains elusive.

In a published article, namely Vol. LVIII of the *Methods in Enzymology*, entitled "New Techniques for Culturing Differentiated Cells: Reconstituted Basement Membrane Rafts" by L. M. Reid and M. Rojkind, cell culture techniques were set forth which were, in essence, attempts to simulate some of the cell-cell relationships and of the tissue matrix relevant to epithelial cells. The techniques described involved the culturing of epithelial cells on substrates of reconstituted basement membrane and in medium supplemented with hormones, serum, and with conditioned medium from feeder layers. That technique, more specifically, involved utilization of reconstituted basement membrane rafts on which were floated epithelial cells over primary cultures of mesenchymal cells normally in association with the epithelial cells. That is, therefore, not applicable to the disclosed technique which involves connective tissue-derived fibers as a substrate for body cells that are normally in contact with basal lamina material, especially differentiated epithelial cells, in cell cultures. Basal lamina material as used herein is a substance found on the surface of differentiated cells, on the basal side or surrounding said cells, and is composed of collagens, carbohydrates including glycosaminoglycans and non-collagenous proteins.

In a published article, namely Vol. 2d. 17 of the *Life Sciences*, entitled "A Simple, Versatile, Nondisruptive Method for the Isolation of Morphologically and Chemically Pure Basement Membranes from Several Tissues" by Elias Meezan, J. Thomas Hjelle, and Klause Brendel, a procedure was set forth for the isolation of intact basement membranes from bovine retinal and brain blood vessels, rabbit renal tubules, and rat renal glomeruli. The techniques described involved a seven step procedure, with several steps utilizing primarily high concentrations of a Sodium Deoxycholate solution, concentrations much higher than in the disclosed technique. Other solutions used in the Meezan procedure contained sodium azide, sodium chloride, and DNase. This procedure differs significantly from the disclosed technique in that using the Meezan procedure, the resultant isolated membranes are partially denatured and not in a form usable by cells in culture. The disclosed technique, however, requires the use of functionally active, non-denatured, connective tissue-derived fibers, and these may only be acquired using the disclosed technique with its different steps, compounds, and concentrations. Another significant distinction is that the disclosed method involves the use of ribonuclease in addition to DNase. The use of ribonuclease and DNase enables the production of truly pure, connective tissue-derived fibers, without any contaminating DNA or RNA, and this is essential for use as a culture substrate. The Meezan procedure does not use Ribonuclease. The use of DNase in the Meezan article to prevent "viscous gel" like DNA from interfering with the isolation procedure would not result in a pure enough or functional product required when using connective tissue-derived fibers as a culture substrate.

SUMMARY OF THE INVENTION

1. Purpose of the Invention

It is an object of the present invention to provide an improved method for the culturing and emplacement of differentiated cells in vivo.

An object of this invention to provide a method for the establishment of in vivo or in vitro cultures of human or animal differentiated cells; the in vitro culture to be subsequently emplaced in vivo.

It is another object of this invention to provide a method as aforesaid in which human or animal differentiated cells are cultured using an extracellular matrix, more specifically, connective tissue-derived fibers, as a substrate.

It is a further object of this invention to provide a method which is applicable to normal cells whatever their degree of differentiation.

It is still a further object of this invention to provide a method which significantly improves the survival and attachment rates for in vivo or in vitro cultures of differentiated cells.

It is still another object of this invention to provide a method which significantly improves the growth properties of in vivo or in vitro cultures of differentiated cells which are capable of growth in vitro or in vivo.

It is still a further object of this invention to provide a method which will permit differentiated cells to retain a significant degree of their differentiated state.

It is still another object of this invention to provide a method which permits certain differentiated cells to retain much of their normal enzymatic activities.

It is still a further object of this invention to provide a method which permits certain differentiated cells to retain to a high degree their ability to secrete substances such as hormones.

It is also an object of this invention to provide a method for the preparation and isolation of a novel culture substrate to be employed for the culturing and/or emplacement of differentiated cells in vivo.

It is another object of this invention to provide tissue-specific connective tissue-derived fibers for the culturing of the related tissue-specific differentiated cells.

It is still a further object of this invention to provide a cell culture environment comprising a plurality of fibers as support for the cells with or without other in vitro solid state support(s) such as a petri dish or test tube, wherein differentiated cells would have an environment more nearly approximating normal tissue conditions when in vitro.

An object is to provide a method for the in vivo culturing of differentiated cells.

An object is to provide a method for the emplacement in vivo of differentiated cells which have been cultured in vitro in the differentiated state.

These and other objects and advantages of the present invention will become evident from the description which follows.

2. Brief Description of the Invention

The present invention basically entails the disclosure of a method and culture solution which enable in vivo emplacement of differentiated cells derived from in vitro culturing of differentiated cells, with significant retention of their differentiated character. In an alternative embodiment, in vivo culturing of differentiated cells is contemplated. Through the use of extracellular matrix fibers, specifically derived from connective tissue, as culture substrates, the method also discloses the isolation of the connective tissue fibers and their preparation as a culture substrate. This method provides significantly higher survival and attachment rates, and often significantly improved growth properties, for in vivo or in vitro cultures of differentiated cells, especially epithelial, over the current methods for culturing these cells. This method also significantly enables certain differentiated cells to retain much of their normal enzymatic activities, and furthermore, this method enables certain differentiated cells to retain to a high degree their ability to secrete substances, such as hormones.

In one embodiment, the present invention is characterized by the provision of a method for in vivo culturing of differentiated cells which entails providing connective tissue-derived fibers including collagens, non-collagenous proteins and carbohydrates as a substrate for an in vivo differentiated cell culture at an in vivo site, whereby the differentiated cell culture remains substantially differentiated and in situ growth of differentiated cells takes place as an in vivo culture at the site. The differentiated cells typically are mammalian cells; usually the differentiated cells are epithelial cells or the like. However, the differentiated cells may be body cells that are normally in contact with basel lamina material. Typically, the connective tissue-derived fibers are isolated from organ tissue, and in a preferred embodiment the resultant in situ growth of the culture of differentiated cells in vivo is bound to cells originally at the in vivo site.

More specifically, one embodiment of the invention entails a method for the in vivo culturing of differentiated cells which includes selecting an in vivo site to be provided with differentiated cells, preparing the site for the receipt of culture medium, and disposing a quantity of culture medium including connective tissue-derived fibers including collagens, noncollagenous proteins and carbohydrates as a substrate for the in situ culturing of differentiated cells onto the in vivo site, whereby in situ growth of differentiated cells takes place as an in vivo culture at the site. Preferably, the resultant in situ growth of the culture of differentiated cells in vivo is bound to cells originally at the in vivo site. Usually, the differentiated cells are mammalian cells; typically, the differentiated cells are epithelial cells. In one embodiment, the differentiated cells are body cells that are normally in contact with basal lamina material. Generally, the connective tissue-derived fibers are isolated from organ tissue or the like.

An alternative embodiment of the invention entails a method for the emplacement in vivo of differentiated cells which is characterized by providing an initial supply of differentiated cells, disposing said initial differentiated cell supply in an in vitro culture medium including collagens, non-collagenous proteins and carbohydrates as a substrate for the in vitro differentiated culture cell, whereby in vitro culturing of the differentiated cells takes place and the differentiated cell culture remains substantially differentiated, and transferring and transplanting or emplacing the resulting growth of differentiated cell culture to an in vivo site to be provided with differentiated cells, so that the supply of differentiated cells at the in vivo site is increased. Generally, the resultant supply in vivo of the growth of the culture of differentiated cells is bound to cells originally at the in vivo site. Typically, the temperature at which the in vitro culturing method is conducted is between 0° C. and 100° C. Preferably, the temperature at which the in vitro culturing method is conducted for mammalian cells is between 29° C. and 42° C. In most instances, the temperature at which the in vitro culturing method is conducted is optimal for the cellular growth in vitro. Usually the differentiated cells in vitro culture remain differentiated for at least one month on the connective tissue-derived fibrous substrate, so long as nutrients for the cells are provided. Preferably, the differentiated cells are mammalian; however, in some instances the differentiated cells may be non-mammalian cells. Typically, the differentiated cells are epithelial cells. In one embodiment, the differentiated cells are body cells that are normally in contact with basal lamina material. In most instances, the differentiated cells are normally-growing cells, and the differentiated cells survive in vitro in a differentiated state. Usually, the connective tissue-derived fibers are isolated from organ tissue or the like.

Preferably, the in vitro aspect of the invention involves placing the connective tissue-derived fibers onto culture solid-state supports in vitro, and allowing the fibers to cover the solid-state supports. In this case, the method usually includes sterilizing the solid-state supports in vitro, after adding the connective tissues-derived fibers. Another further aspect entails adding the differentiated cells to the tissue culture plates in vitro after sterilization. Typically, the connective tissue-derived fibers attach to the solid-state support in vitro.

In preferred embodiments, certain differentiated cells in vitro culture exhibit a growth rate of at least 300%, as measured by the rate of the number of differentiated cells after one month, to the number of differentiated cells that attached day 1 of the culture. In this case, preferably certain differentiated cells in in vitro culture exhibit a growth rate of about 1000% as measured by the ratio of the number of differentiated cells after one month to the number of differentiated cells that attached day one of the in vitro culture. Typically, the time period the differentiated cells in in vitro culture remain essentially differentiated is at least about one month, and is proportional to the presence of the fibrous substrate and nutrients for the cells. In general, the attachment efficiency of differentiated cells of the in vitro culture is at least 50%, and preferably the attachment efficiency of the differentiated cells of the in vitro culture is up to and including 86%.

The techniques for the in vitro culturing of the differentiated cells are amply elucidated in the cited U.S. patent application Ser. No. 089,167 filed Oct. 29, 1979, to issue Oct. 5, 1982 as U.S. Pat. No. 4,352,887, to which those skilled in the art are referred, for an exemplary teaching of the contemplated techniques. The disclosures of this cited application Ser. No. 089,167, to issue as U.S. Pat. No. 4,352,887, are hereby incorporated and embodied herein by cited reference, to serve as further support for an understanding by the reader of the present invention. This is especially true with regard to the exemplary data tables, test results, and Examples in the cited copending reference of common ownership.

Thus, in the present invention, a socio-cell culture technique is disclosed which is applicable to both in vivo culturing of differentiated cells, so as to promote organ growth and replacement or the like, and in vitro culturing of differentiated cells followed by emplacement and/or grafting of the resultant growth of cell culture into and onto the organ or tissue to be repaired, built up, or replaced. The method entails a culture medium for differentiated mammalian cells. It is very difficult to culture differentiated cells outside of the body, e.g. a human body or other viable living organism. The present culture medium replicates what the differentiated cells grow in, in the body, e.g., connective fibers, etc., all in vitro or in an alternative embodiment, the present culture medium accomplishes in vivo culturing of differentiated cells, i.e. cell, organ, or tissue growth in vivo.

Thus, in the present invention, the differentiated cells are bound to a matrix, for culture and growth. Then the cells are implanted in an animal or person, and the cells are grown in vivo. For example, pancreatic cells are taken and emplaced in an in vitro culture medium of the present invention. Then further cells plate out on the original cells, and the entire cell culture growth is put under in vivo conditions into the functioning alive body or organism, either human or animal but typically mammalian, and the cells still function. Other types of differentiated cells are contemplated as being within the scope of the present invention. For example, cells could be emplaced under the skin or in the peritoneum, in the stomach wall, or at other appropriate sites in the body, and the implanted cells will function along with original in situ cells. In prior art techniques, cells taken out of the body or organism lose their identity. In the present invention; e.g. liver cells remain in vitro as liver cells, and this culture medium concept is used clinically as a type of transplant technique. Thus, a set of cells is taken from the patient, e.g. a person who has liver trouble. What is taken is some good and well functioning remaining liver cells. These are grown in vitro on the matrix, and are subsequently emplaced back into the diseased liver, where they function normally, with no rejection because the cells of the culture growth are the person's own cells. What can be used is either the person's own cells, or a syngeneic transplant, which means cells, e.g. from identical twins. The opposite of this is an allogeneic transplant, where the cells are derived from a donor who is not the same type of person and there are some genetic differences.

When chemists want to identify an active factor, they normally use a solution to extract out that factor from the raw material. Factor is now in solution with other things. In solution, the use standard chromatographic methods the factor can be weaned away from the contaminants and impurities. All of that scenario is dependent on solubilization of the active factor, i.e. to get it into solution. The present matrix, whatever the form, is cross-linked and consequently highly insoluble and precludes dissolving in solution (might get one component out but not all).

The present invention goes in the opposite direction, using a negative selection method: solubilize away that which is presumed not wanted and then left with insoluble matrix. Not only biologically active material, but also contaminants are insoluble, so the material isolated will be a mixture of active and inactive factors. It means, also, there are many methods to get out components, e.g. variable concentration of salt solutions. Solutions chosen for extraction are ones in which collagens do not dissolve and are insoluble. Concentration is usually one molar sodium chloride, but one could use 1.5 molar, 3 molar, etc., concentrations may vary, and still have active components.

The present invention is thus basically an in vivo concept, utilizing these methods supra, and the matrix can be prepared in a number of forms, e.g. a powder, as mechanically dispersed and form utilized in plastic surgery for repair, regeneration of tissues, or any method in which particular cell types are desired to grow and function. Application methods for emplacement of the culture growth into the organ, tissue, organism, site, or substrate include pasting into, sprinkling onto, or gel it on, a powder, a mesh (fibrous) or a gel. In summary, the technique should have a mixture of three components, namely anchorage proteins, proteoglycans, and collagens and other non-collageneous proteins, which are in association with the collagens (non-identified factors). In summary, the present invention contemplates the extension of the methods and techniques described in accordance with the related U.S. patent applications mentioned supra, which cited U.S. patent applications are incorporated into the present disclosure by reference, to either the in vivo culturing of differentiated cells in humans or animals, or to the in vitro culturing and growth of differentiated cells, followed by the transplanting and emplacement in vivo of the cell culture growth into a living organism, e.g. an organ or tissue of a living human being.

The invention accordingly consists in the features of construction, combination of elements, and series of steps which will be exemplified in the method hereinafter described and of which the scope of application is as elucidated supra and as will be indicated in the appended claims.

DETAILED DESCRIPTION OF THE PREFERRED EMBODIMENTS

Broadly stated, the method and the culture dish of the present invention are for in vivo or in vitro culturing of differentiated cells, comprising inter alia the in vitro cell culture utilization of substrates, whereby differentiated cell cultures retain a significant degree of their differentiated state.

Stated in more specific terms, the present invention comprises a method and, e.g., a culture plate for in vitro culturing of mammalian differentiated cells. This comprises providing connective tissue-derived fibers as a cell culture substrate which is either suspended in a solution or attached to a culture plate or other solid state support, whereby differentiated cells present on said solid state support or in solution may grow in number over time while substantially retaining their differentiated state.

By the term "connective tissue-derived fibers" as used hereinbefore and hereinafter through the specification and claims, it is meant a substance derived from connective tissues of humans or animals which is composed from materials selected from the group consisting of collagens, non-collagenous proteins, and carbohydrates.

A method for preparation and isolation of connective tissue-derived fibers for use in a cell culture includes:

a. dispersing tissue to form a suspension of connective tissue-derived fiberous solids;

b. separating the connective tissue-derived fiberous solids out of the suspension of step a and adding said solids to a delipidation solution;

c. separating the connective tissue-derived fiberous solids out of the solution of step b and adding said solids to a saline solution containing DNase and Ribonuclease; and e. separating the connective tissue-derived fiberous solids out of the solution of step d and rinsing said solids, first with a saline solution and then with the solution to be used in the culture.

Separation of the solids from the suspension may be by centrifugation or filtration. In addition, the isolated connective tissue-derived fibers may be stored frozen with a cryoprotective agent or sterilized and stored at temperatures above freezing. The delipidation solution may be a detergent, Butanol/ether mixture, or other delipidation solutions.

More specifically, this method comprises:

a. mincing and homogenizing tissue in a volume of water at about 1°–10° C. to form a suspension of connective tissue-derived fiberous solids;

b. separating the connective tissue-derived fiberous solids from the solution of step a;

c. collecting the connective tissue-derived fiberous solids of step b and adding said solids to a quantity of water;

d. blending the mixture of step c for about one hour at about 1°–10° C.;

e. separating the connective tissue-derived fiberous solids from the solution of step d and rinsing the solids with a salt solution;

f. blending the mixture of step e for about one hour at about 1°–10° C.;

g. separating the connective tissue-derived solids from the solution of step f;

h. observing the solution of step g and repeating steps e, f and g until said solution of step g is clear;

i. adding the connective tissue-derived solids of step g to an amount of serum-free medium equal to about half the amount of tissue used to step a;

j. adding DNase and ribonuclease to the serum-free medium of step i at a ratio of about 1 mg:50 ml and 5 mg:50 ml, respectively;

k. blending the mixture of step j for about 1 hour at about 30°–45° C.;

l. separating the connective tissue-derived fibrous solids from the solution of step k and staining a sample of said solids with nucleic acid stain;

m. repeating steps i, j, k and l until said sample stain indicates nucleic acids are removed;

n. rinsing the connective tissue-derived fibrous solids of step 1 in a salt solution for at least about 0.5 hour;

o. separating the connective tissue-derived fibrous solids from the solution of step n and adding said solids to a delipidation solution;

p. stirring the mixture of step o for about one hour;

q. separating the connective tissue-derived fibrous solids from the solution of step p and washing them with water at least about one time;

r. adding the connective tissue-derived fibrous solids of step q to serum-free medium, keeping said mixture at about 1°–10° C. while stirring said mixture for about 12 hours; and s. separating the connective tissue-derived fibrous solids from solution of step r whereby the solids are connective tissue-derived fibers ready to use in cultures as a culture substrate.

Preferably, this method comprises:

a. mincing tissue and homogenizing by hand or in a Waring blender, using 5–10 vol of cold distilled water per gram of tissue, while keeping sample at about 4° C. to form a suspension of connective tissue-derived fiberous solids. The preferable amount of starting material is about 100 grams;

b. immediately filtering through a filter, preferably polyester, into a 2- to 4-liter beaker placed in ice;

c. collecting connective tissue-derived fibrous solid filtrate on top of the polyester filter and putting said filtrate into a beaker with water, then washing polyester filter thoroughly and adding the wash to the beaker;

d. stirring the solution of step c for about 1 hour at about 4° C.;

e. filtering the solution of step d through polyester and then repeating step c, using 0.1–1.0M NaCl;

f. stirring the solution of step f for about 1 hour at about 4° C.;

g. collecting the connective tissue-derived fiberous/solid precipitate from the solution of step f by filtration through the polyester filter. If the solution is very opaque, repeat steps e–g until the solution is clear;

h. putting the connective tissue-derived fiberous solid precipitate retained on the filter into a small amount of serum-free medium (about 30–50 ml/100 g of starting material) and add about 1.0 mg of DNase and about 5 mg of ribonuclease per 50 ml of serum-free medium;

i. stir the solution of step h for about 1 hour at about 37° C.;

j. stirring a sample of the connective tissue-derived fiberous solid precipitate of step i with Acridine Orange (0.3% in distilled water). The nucleic acid contaminants stain an intense orange with this solution. Precipitate reasonably free of these contaminants will stain a pale salmon color. Repeating steps h-j until the precipitate is clean of nucleic acid components;

k. collecting connective tissue-derived fibrous solid precipitate of step j by filtration and rinsing said precipitate in 0.1–1.0M NaCl or in serum-free medium for about 0.5 hour;

l. collecting connective tissue-derived fibrous solid precipitate of step k by filtration and add to 100 ml of distilled water over which is layered an equal volume of about a 40:60 Butanol/ether solution. The mixture is then stirred about every 5 min for 0.5–1 hour at about room temperature;

m. sampling the connective tissue-derived fibrous solid precipitate of step l and adding to an oil red O solution. If translucent red globules are present, repeat step l and m until they disappear. The translucent red material would appear within 3–5 min.;

n. collecting the connective tissue-derived fibrous solid precipitate by filtration and wash with 250 ml of distilled water at least about three times (about 1 hour each), separating connective tissue-derived fibrous solids from solution between washings;

o. stirring the connective tissue-derived fibrous solid precipitate overnight in PBS or serum-free medium (1X 10 volume) at abut 4° C.; and p. collecting the connective tissue-derived fibrous solid precipitate connective tissue-derived fibers by filtration and either using immediately for culture or chemical studies or store by freezing at −20° C. in serum-free medium plus 10% glycerol.

Oil red O used in the procedure above, comprises 0.5% in 60% isopropanol (stock solution). For use, dilute 6 parts stock to 4 parts water, mix on a vortex, and filter.

In a more specific aspect of this invention, the method comprises:

a. isolation of connective tissue fibers from organ tissue;

b. placing connective tissue fibers onto solid-state supports and spreading them over the solid-state support, or placing the connective tissue fibers into solution and mixing them in suspension;

c. sterilizing the solid-state support or solution after adding the connective tissue fibers;

d. adding the differentiated cells desired to be cultured in vitro to the solid-state support or solution;

e. providing an operating temperature optimal for those cells; and f. transplanting and emplacing the resulting differentiated cell culture in vivo.

The immediately aforesaid method enables differentiated epiehelial cells to retain a significant degree of their differentiated state in the culture for as long as one month or longer, so long as nutrients adequate to insure the survival of the cultured cells over this longer period are supplied.

In a preferred aspect of this invention, the method comprises:

a. isolation of connective tissue fiber from liver tissue;

b. placing connective tissue-derived fibers onto the solid-state support and spreading the fibrous matrix to cover said solid-state support wherein the cells are to be cultured;

c. sterilizing the solid-state support after adding the connective tissue-derived fibers;

d. adding differentiated cells desired to be cultured in vitro to the solid-state support;

e. providing an operating temperature optimal for these cells and between 0° and 100° C.; and f. subsequently transplanting the resultant differentiated cell culture growth into a viable living in situ liver.

It is to be borne in mind that pursuant to the present invention, the human or animal differentiated cells may be cultured on a matrix derived from the same organ as the cells to be cultured, but not necessarily derived from the same species.

Another aspect of the present invention relates to a method for in vitro culturing of differentiated cells comprising:

a. isolating connective tissue-derived fibers from organ tissue; and b. providing the fibers as a substrate for an in vitro differentiated cell culture.

The immediate aforesaid method has been found to permit the differentiated cells in the in vitro culture to remain substantially in their differentiated state. The immediate aforesaid method is operable and could be conducted at a temperature appropriate to the cells of interest.

It is an important aspect of this invention that the time period that the immediate aforesaid method permits differentiated cells to remain in their substantially differentiated state for at least one month or longer, so long as appropriate nutrients, hormones, growth factors, and transfer factors (either pure or in the form of sera or plasma) are supplied to insure the survival of the cells in culture. This method also provides an attachment efficiency for the differentiated epithelial cells in vivo and in vitro that is significantly greater than in the absence of the proposed connective tissue-derived matrix.

The preferred embodiment of this method comprises providing tissue culture articles of various sorts precoated with the organ-specific connective tissue-derived fiber matrix. The preferred embodiment of this method is operable for cell maintenance at temperatures optimal for the cells, between 0° C. and 100° C.

Another aspect of the present invention relates to a cell culture environment which comprises tissue-specific connective tissue-derived fibers in suspension within a solution. The tissue-specific fibers are from organ tissues and are placed in suspension in a solution further comprising a medium supplemented with cell-specific hormones or with plasma or serum (or with a combination of any of them) and with conditioned medium from cultures of mesenchymal cells or with factors derived from them.

The term "conditioned medium" as used herein is a medium in which other cells have been previously cultured and which has been subsequently filtered and into which certain cellular by-products of the initial cell culture has been incorporated. The cellular by-products which had been incorporated into said conditioned medium by the initial cell culture, if isolated, are what is meant by use of the term "factors derived from culture of mesenchymal cells." The solution is operable for cell growth at temperatures optimal for their growth between 0° and 100° C.

It thus will be seen that there is provided a method for the culturing and emplacement of differentiated cells in vivo (any prior in vitro culturing being in accordance with the U.S. patent applications cited supra), which achieves the various objects of the invention, and which is well adapted to meet the conditions of practical use.

As various possible embodiments might be made of the above invention, and as various changes might be made in the embodiments above set forth, it is to be understood that all matter herein described is to be interpreted as illustrative and not in a limiting sense. Thus, it will be understood by those skilled in the art that although preferred and alternative embodiments have been described in accordance with the Patent Statutes, the invention is not limited thereto or thereby, since the embodiments of the invention particularly disclosed and described herein above are presented merely as an example of the invention. Other embodiments, forms, and modifications of the invention, coming within the proper scope and spirit of the appended claims, will of course readily suggest themselves to those skilled in the art. Thus, while there has been described what is at present considered to be the preferred embodiments of the invention, it will be obvious to those skilled in the art that various changes and modifications may be made therein, without departing from the invention, and it is, therefore, aimed in the appended claims to cover all such changes and modifications as fall within the true spirit and scope of the invention.

What is claimed is:

1. A method for providing an improved in vivo site for promoting the growth of site-specific differentiated cells, comprising providing site-specific connective tissue-derived fibers comprising collagens, non-collagenous proteins and carbohydrates as a substrate for in vivo cell culture of site-specific differentiated cells at the site.

2. The method of claim 1 in which the site-specific differentiated cells are mammalian cells.

3. The method of claim 1 in which the site-specific differentiated cells are epithelial cells.

4. The method of claim 1 in which the site-specific differentiated cells are body cells that are normally in contact with basal lamina material.

5. The method of claim 35 in which the site-specific connective tissue-derived fibers are isolated from organ tissue.

6. A method for the in vivo culturing of site-specific differentiated cells which comprises selecting an in vivo site to be provided with site-specific differentiated cells, preparing said site for the receipt of culture medium, and disposing a quantity of culture medium comprising site-specific connective tissue-derived fibers comprising collagens, non-collagenous proteins and carbohydrates as a substrate for the in situ culturing of site-specific differentiated cells at said in vivo site, and applying differentiated cells to the culture medium whereby in situ growth of site-specific differentiated cells takes place.

7. The method of claim 6 in which the resultant in situ growth of the culture of site-specific differentiated cells in vivo is bound to cells originally at the in vivo site.

8. The method of claim 6 in which the site-specific differentiated cells are mammalian cells.

9. The method of claim 6 in which the site-specific differentiated cells are epithelial cells.

10. The method of claim 6 in which the site-specific differentiated cells are body cells that are normally in contact with basal lamina material.

11. The method of claim 6 in which the site-specific connective tissue-derived fibers are isolated from organ tissue.

12. A method for the emplacement at an in vivo site of site-specific differentiated cells which comprises providing an initial supply of site-specific differentiated cells, disposing said initial supply in an in vitro culture medium comprising site-specific collagens, non-collagenous proteins and carbohydrates as a substrate for the in vitro cell culture, whereby in vitro culturing of said site-specific differentiated cells takes place and the cell culture remains substantially differentiated, and transferring and transplanting the resulting growth of the site-specific differentiated cell culture to said in vivo site to be provided with site-specific differentiated cells, so that the supply of differentiated cells at said in vivo site is increased.

13. The method of claim 12, wherein the temperature at which the in vitro culturing method is conducted is optimal for the cellular growth in vitro.

14. The method of claim 12, wherein the site-specific differentiated cells are mammalian.

15. The method of claim 12, wherein the site-specific differentiated cells are non-mammalian cells.

16. The method of claim 12, wherein the site-specified differentiated cells are epithelial cells.

17. The method of claim 12, wherein the site-specific differentiated cells are body cells that are normally in contact with basal lamina material.

18. The method of claim 12, wherein the site-specific connective tissue-derived fibers are isolated from organ tissue.

19. The method of claim 12, further comprising placing the site-specific connective tissue-derived fibers onto culture solid-state supports in vitro, and allowing said fibers to cover said solid-state supports.

20. The method of claim 19, further comprising sterilizing said solid-state supports in vitro, after adding the site-specific connective tissue-derived fibers.

21. The method of claim 20, further comprising adding the site-specific differentiated cells to the tissue culture plates in vitro after sterilization.

22. The method of claim 20, wherein the site-specific connective tissue-derived fibers attach to the solid-state support in vitro.

* * * * *